(12) United States Patent
Kirchhuebel

(10) Patent No.: US 7,367,674 B2
(45) Date of Patent: May 6, 2008

(54) PERIMETER AND A METHOD FOR OPERATING A PERIMETER

(75) Inventor: Rainer Kirchhuebel, Asslar (DE)

(73) Assignee: Oculus Optikgeraete GmbH, Wetzlar Dutenhofen (DE)

( * ) Notice: Subject to any disclaimer, the term of this patent is extended or adjusted under 35 U.S.C. 154(b) by 77 days.

(21) Appl. No.: 11/352,042

(22) Filed: Feb. 9, 2006

(65) Prior Publication Data

US 2006/0181680 A1     Aug. 17, 2006

(30) Foreign Application Priority Data

Feb. 11, 2005  (DE) ............... 10 2005 006 603
Apr. 12, 2005  (DE) ............... 10 2005 016 945

(51) Int. Cl.
*A61B 3/02*     (2006.01)

(52) U.S. Cl. ............... 351/224; 351/223; 351/237

(58) Field of Classification Search ........ 351/222–224, 351/237, 239, 246
See application file for complete search history.

(56) References Cited

U.S. PATENT DOCUMENTS 4,429,961 A    2/1984   Sheingorn
4,634,243 A    1/1987   Massof et al.
5,036,500 A *  7/1991   Ganter ............... 368/47

FOREIGN PATENT DOCUMENTS

DE    31 43 880 A1    9/1982
DE    37 31 415 A1    4/1989
DE    689 27 478 T2   8/1989

OTHER PUBLICATIONS

Carl Zeiss Meditec AG, Projektionsperimeter HFA II-*i*. Präzision und Zeitgewinn.(brochure), pp. 1-6, Deutschland May 2003.

* cited by examiner

*Primary Examiner*—Huy K Mai
(74) *Attorney, Agent, or Firm*—Blakely, Sokoloff, Taylor & Zafman LLP

(57) ABSTRACT

The invention relates to a perimeter and a method for operating a perimeter during a field of vision examination, whereby light stimuli in the field of vision of the person to be tested are presented on an observational surface during the examination process. At least one moving light stimulus is presented to the eye during an examination process with a time offset and then at least one non-moving light stimulus or conversely is presented on the observational surface.

18 Claims, 1 Drawing Sheet

PERIMETER AND A METHOD FOR OPERATING A PERIMETER

FIELD

The present invention relates to a perimetric test method according to the preamble of claim 1. In addition, the present invention also relates to a perimeter suitable for implementing this method.

BACKGROUND

The science of perimetry relates to testing the field of vision of the eye. When such tests are performed regularly, certain diseases and/or disease courses can be detected and/or observed.

Known perimeters have an observational surface, which is designed in the manner of a hemispherical shell, for example, and forms a concave projection surface in the interior. The patient to be examined looks into the concave hemisphere, with the eye that is to be tested being situated at the center of the hemisphere. As soon as the eye to be tested is positioned at the center of the hemisphere, the patient is instructed to keep his eyes on a fixation mark at the center of the projection area of the hemisphere. Once this has been done properly, the sensitivity of the eye to stimuli in the field of vision is tested and recorded. This is done by presenting light stimuli at various locations on the observational surface, while the patient reports in each case, e.g., by depressing a switch, whether or not the corresponding light stimulus has been observed. As a result, the sensitivity of the eye to light stimuli at various locations in the field of vision can be determined and mapped.

Two fundamentally different perimetric test methods are known from the state of the art. In the first variant, so-called static perimetry, non-moving light stimuli are presented to the patient. By varying the luminous density of these light stimuli, the stimulus threshold at a certain location in the field of vision can be ascertained, for example. In addition to static perimetry, there is also the known kinetic perimetry, in which the patient is presented with moving light stimuli, with a point of light being guided along a predetermined line of movement over the observational surface, for example. The limits of peripheral vision can be determined by kinetic perimetry in particular.

Both static and kinetic field of vision examinations can be performed using known perimeters because the moving and/or non-moving presentation of light stimuli requires completely different perimeter designs. However, recent studies have shown that describing a patient's field of vision by static perimetry on the one hand and/or by kinetic perimetry on the other hand remains incomplete in either case. Both examination methods have advantages and disadvantages and neither, when taken alone, can completely describe the condition of the field of vision.

SUMMARY

Against the background of this state of the art, the object of the present invention is therefore to propose a novel method for operating a perimeter during a field of vision test so that more accurate test results can be obtained. In addition, another object of the present invention is to propose a perimeter suitable for implementing this method.

This object is achieved by a method and a perimeter according to the teaching of the two independent main claims.

Advantageous embodiments of the present invention are the object of the subclaims.

The basis idea of the inventive method is that at least one moving light stimulus is presented to the eye during a test with a time offset, and thereafter at least one non-moving light stimulus is presented or vice versa, first at least one non-moving light stimulus and then at least one moving light stimulus being presented to the observational surface. As a result, the advantages of static perimetry are combined with the advantages of kinetic perimetry in one examination process. Therefore, the field of vision examination can be performed in a time-optimized manner because static perimetry and kinetic perimetry need not be performed in separate examinations one after the other in a time-consuming manner. Performing the two test methods on separate equipment units also has the disadvantage that the boundary conditions of the separate examination procedures, e.g., the fixation of the eye and the position of the eye as well as the patient's constitution undergo changes so that the results of the examination are falsified.

To allow the most thorough possible examination and mapping of a patient's field of vision, a multitude of light stimuli must be presented to the patient. In order to be able to perform the test method with the greatest possible efficiency, it is therefore now particularly advantageous if the moving light stimuli and the non-moving light stimuli are combined to form one or more groups, whereby these groups of moving light stimuli and non-moving light stimuli are then presented one after the other on the observational surface.

Field of vision examinations should be as relevant to reality as possible. At the center of the field of vision, it is mainly the cone sensitivity that is important; this can be tested especially well by static perimetry. The rods are responsible mainly for receiving light signals in the periphery of the field of vision, i.e., at the edges of the reticulum, where the rods are interconnected over a large area. Rod sensitivity is preferably tested by kinetic perimetry. It is therefore especially advantageous if non-moving light stimuli are presented at the center of the field of vision and moving light stimuli are presented at the periphery of the field of vision so that the rods and cones on the retina can be evaluated by the optimum test method in each case. This type of examination also comes very close to the profile of requirements for using the eyes in reality because moving objects usually come from the edge of the field of vision and must be detected very rapidly by the human eye. In highway traffic there are situations in which a ball rolls onto the road, for example, and a child runs after it. The ball, moving from the outside, thus enters the field of vision of the driver, who then concentrates mainly at the center in looking straight ahead. However, there are more static objects to be seen at the center of the field of vision, which can preferably be tested by static perimetry.

The light sensitivity of the retina to moving and non-moving light stimuli is fundamentally different. The presentation of non-moving light stimuli should therefore be accomplished with a different luminous density profile than presentation of moving light stimuli. It should be noted that non-moving light stimuli are regularly recognized better, which is why non-moving light stimuli should preferably be presented with a darker luminous density profile, whereas moving light stimuli should be presented with a brighter luminous density profile.

In addition, it should be noted that the light sensitivity of the retina of various patients is at a stimulus level that must be determined individually in each case. It is therefore advantageous for the light sensitivity of the retina of the individual patient's eye to be determined before performing the perimetric examination. During the perimetric examination, the luminous density profile of the moving and non-moving light stimuli is coordinated with the individual light sensitivity profile of the retina and adjusted accordingly.

In particular, static perimetry makes it possible to detect so-called threshold values above which a patient can perceive a light stimulus. In the presentation of non-moving light stimuli, it is therefore especially advantageous if light stimuli below the stimulus threshold and light stimuli above the stimulus threshold are presented at a certain point in the field of vision. To do so, the luminous density of the light stimulus may be increased continuously, for example, in which case the threshold value is then determined from the time when the patient first perceives the light stimulus.

In presenting of moving light stimuli, it is preferable to work with preselected test spot size with adjusted brightness. Test spot sizes according to Goldmann III, 1 are especially suitable.

In the inventive method, moving and non-moving light stimuli are presented in succession or conversely, non-moving and moving light stimuli are presented. This may be accomplished in particular by forming groups of moving light stimuli and groups of non-moving light stimuli. In the transition between presentation of moving and non-moving light stimuli to presentation of non-moving and moving light stimuli respectively, there should preferably be a brief examination pause in each case. During this examination pause, it is in particular also possible to make changes and adjustments in the perimeter to switch the perimeter between static and kinetic perimetry and conversely between kinetic and static perimetry. For example, the examination pause makes it possible to insert, remove or change a correction glass at the perimeter, so as to adjust the perimeter for static perimetry or for kinetic perimetry, depending on the test method to be pursued subsequently. For the accuracy of the test results, it is of enormous importance for correct fixation of the eye in the proper position during the examination process to be ensured. Fixation of the eye in the correct position should be checked at least once during the examination process to verify the accuracy of the test results thus obtained.

Checking for correct fixation in the proper position is preferably performed by presenting a light stimulus to the eye at the center of the field of vision, where the light stimulus has such a high luminous density that it can be perceived by the patient in any case. If this light stimulus is not perceived by the patient despite this high luminous density of the light stimulus presented at the center of the field of vision, it may be assumed that the patient's eye has not been held at the center of the field of vision. Alternatively, a light stimulus may also be presented to the patient in the area of the blind spot in the field of vision. If the patient perceives this light stimulus despite its being presented in the area of the blind spot, it may be assumed that the patient's eye is not held in the proper position.

The inventive method permits combined used of static and kinetic perimetry. It is of course possible here for the perimetric test results derived from the presentation of the non-moving light stimuli (static perimetry) and the presentation of the moving light stimuli (kinetic perimetry) to be output separately. However, a much more relevant evaluation of a patient's field of vision can be achieved by displaying the statically determined perimetric examination results and the kinetically determined perimetric examination results in a joint presentation of results, e.g., a corresponding graph.

In presenting the results, preferably isopter points, i.e., perception of identical brightness and/or point size or isopter lines, i.e., lines of identical perception of brightness and/or line size can be displayed. As an alternative and/or in addition to this isopter display, single point results may also be displayed, in particular single point results determined by static perimetry.

In performing the method, the examiner should have the option, after the display of results, of a specific follow-up examination of individual areas of the field of vision for reviewing and correcting the display of results. The results of this follow-up examination should then be entered directly into the display of results to correct the display of results as a function of the result of the follow-up examination.

For documentation purposes, in a preferred variant of the process, the display of results should be stored in a memory device, e.g., on a hard drive. Storing the test results makes is possible to compare subsequent test results with previous test results in particular.

The comparison of test results is simplified in particular by the jointly displaying at least two displays of results, each being the result of tests performed at different points in time. To do so, the isopter points, isopter lines or individual point results of different test runs, for example, can be displayed jointly on a display screen or printed out jointly on a printer. By comparing the individual test results and the differences thereby found, progressive disease courses can be documented and recognized very well.

To perform the inventive method, a perimeter is proposed in which the light stimuli can be presented to the observational surface as optionally moving and non-moving light stimuli.

BRIEF DESCRIPTION OF THE DRAWINGS

The present invention is explained in greater detail below on the basis of the drawing as an example.

It shows.

DETAILED DESCRIPTION

Figure 1:
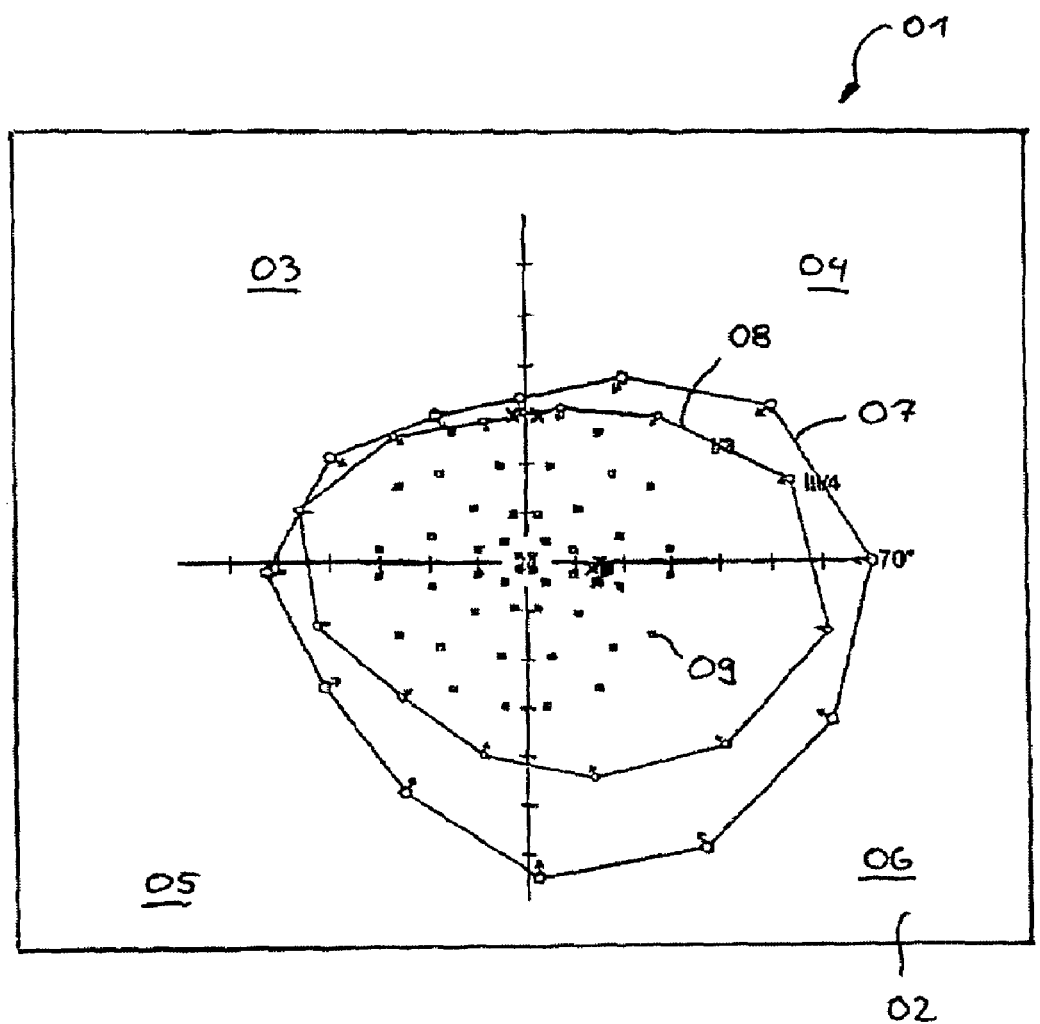
FIG. 1 the display of results of two perimetric tests performed with an interval of time between them using the inventive method.

FIG. 1 shows the display of results 01 of two perimetric tests performed using the inventive method with an interval of time between them. The field of vision 02 of the patient being examined, as represented in the display of results 01, is subdivided into four quadrants 03, 04, 05 and 06.

In performing the perimetric examinations, a group of non-moving light stimuli were presented to the patient at least at the center of the field of vision 02. The results of this static perimetry are plotted as individual points 09 in the display of results 01, with individual points 09 belonging to the tests performed at the various points in time being displayed graphically, e.g., by using different colors.

Then after the presentation of the non-moving light stimuli, a group of moving light stimuli distributed over the four quadrants of the field of vision 02 was presented to the patient. The results of this kinetic perimetry of the two tests performed at different points in time are plotted as isopter lines 07 and 08 in the display of results 01. The isopter lines are lines of the same light stimulability on the patient's retina.

The course of the disease in the area of the peripheral field of vision can be recognized very well by a comparison of the isopter lines 07 and 08 because the isopter line 08 which corresponds to the kinetic perimetry at a later point in time is definitely smaller in comparison with the isopter line 07 corresponding to the kinetic perimetry at an earlier point in time. In other words, this means that the patient's peripheral field of vision has definitely grown smaller between the two examinations at different points in time.

By displaying the individual points 09, which represent the result of the static perimetry, and the isopter lines 07 and/or 08, which represent the result of kinetic perimetry, in a common display of results 01, the treating physician is provided with a complete overview of the condition of the retina. This test provides results that are extremely realistic because the light stimulability in the periphery of the field of vision 02 was determined with moving light stimuli and the light stimulability at the center of the field of vision 02 was determined with non-moving light stimuli.

What is claimed is:

1. A method for operating a perimeter during a field of vision examination, comprising:
   presenting light stimuli in the field of vision of the person to be tested on an observational surface of a hemispherical shell during an examination process, wherein at least one moving light stimulus on the observational surface is presented to the eye during an examination process and at least one non-moving light stimulus is presented, the presentation of the at least one moving light stimulus and the at least one non-moving light stimulus separated by a time offset; and
   receiving a user response to the light stimuli.

2. The method according to claim 1, wherein a group of moving light stimuli is presented on the observational surface and then a group of non-moving light stimuli is presented or vice versa.

3. The method according to claim 1, wherein non-moving light stimuli are presented to the eye at the center of the field of vision and at the periphery of the field of vision moving light stimuli are presented on the observational surface.

4. The method according to claim 1, wherein the non-moving light stimuli and the moving light stimuli are presented with different luminous density profiles on the observational surface.

5. The method according to claim 4, wherein the non-moving light stimuli are presented on the observational surface with a darker luminous density profile and the moving light stimuli are presented with a lighter luminous density profile.

6. The method according to claim 4, wherein the light sensitivity of the retina of the eye is determined, the luminous density profile of the light stimuli being varied as a function of the light sensitivity of the retina.

7. The method according to claim 1, wherein for a determination of a threshold value, a non-moving light stimulus with a luminous density below the stimulus threshold is presented at least once on the observational surface.

8. The method according to claim 1, wherein the moving light stimuli have a predetermined test spot size with an adjusted brightness, in particular corresponding to the test spot size according to Goldmann III, 1.

9. The method according to claim 1, wherein a short examination pause is observed between the presentation of the moving light stimuli and the presentation of the non-moving light stimuli, in particular between the presentation of a group of moving light stimuli and a group of non-moving light stimuli.

10. The method according to claim 9, wherein the time offset lasts at least long enough for a correction lens to be inserted, removed or replaced at the perimeter during the testing pause.

11. The method according to claim 1, wherein fixation of the eye in the proper position is checked during the examination process.

12. The method according to claim 11, wherein the check for fixation of the eye in the proper position during the examination process is performed by presentation of a light stimulus in the area of the center of the field of vision or by presentation of a light stimulus in the area of the blind spot.

13. The method according to claim 1, wherein the static perimetric examination result derived from the presentation of the non-moving light stimuli and the kinetic perimetric test result derived from the presentation of the moving light stimuli are displayed in a joint display of results (01), in particular a graph of results.

14. The method according to claim 13, wherein isopter points (09) or isopter lines (07, 08) are displayed in the display results.

15. The method according to claim 13, wherein after presentation of the display of results (01), individual areas of the field of vision are examined again in a targeted manner to check on and correct the display of results, whereby the display of results is varied as a function of the result of the follow-up examination.

16. The method according to claim 13, wherein the display of results (01) can be stored in a memory device.

17. The method according to claim 13, wherein at least two displays of results, each showing the result of test processes conducted at different points in time, are displayed jointly, in particular or displayed on a display screen and/or printed out with a printer.

18. The method according to claim 1, wherein moving light stimuli and non-moving light stimuli can be presented on the observational surface of the perimeter.

* * * * *